(12) United States Patent
Akiba

(10) Patent No.: US 8,821,381 B2
(45) Date of Patent: Sep. 2, 2014

(54) ELECTRONIC ENDOSCOPE

(75) Inventor: Kazuyoshi Akiba, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 1318 days.

(21) Appl. No.: 12/065,195

(22) PCT Filed: Aug. 31, 2006

(86) PCT No.: PCT/JP2006/317203
§ 371 (c)(1),
(2), (4) Date: Feb. 28, 2008

(87) PCT Pub. No.: WO2007/026815
PCT Pub. Date: Mar. 8, 2007

(65) Prior Publication Data
US 2009/0253955 A1 Oct. 8, 2009

(30) Foreign Application Priority Data

Sep. 2, 2005 (JP) ................................ 2005-255415

(51) Int. Cl.
*A61B 1/04* (2006.01)
*A61B 1/00* (2006.01)
*A61B 1/06* (2006.01)
*A61B 1/05* (2006.01)

(52) U.S. Cl.
CPC ............... *A61B 1/05* (2013.01); *A61B 1/00105* (2013.01); *A61B 1/053* (2013.01)
USPC ............ 600/110; 600/129; 600/112; 600/172

(58) Field of Classification Search
CPC .............................. A61B 1/05; A61B 1/00096
USPC ......... 600/110, 166, 129, 167, 168, 111, 112, 600/103, 173, 117, 101, 130, 109, 172, 600/175; 348/75, 72; 359/771, 754
See application file for complete search history.

(56) References Cited

U.S. PATENT DOCUMENTS

| 4,677,471 | A | * | 6/1987 | Takamura et al. | 348/76 |
| 4,706,654 | A | * | 11/1987 | Ogiu et al. | 600/130 |
| 4,741,327 | A | * | 5/1988 | Yabe | 600/130 |
| 4,745,470 | A | * | 5/1988 | Yabe et al. | 348/76 |
| 4,745,471 | A | * | 5/1988 | Takamura et al. | 348/76 |

(Continued)

FOREIGN PATENT DOCUMENTS

| JP | S62-96614 | 6/1987 |
| JP | 2000-014635 | 1/2000 |
| JP | 2003-260029 | 9/2003 |

*Primary Examiner* — John P Leubecker
*Assistant Examiner* — Ronald D Colque
(74) *Attorney, Agent, or Firm* — Scully, Scott, Murphy & Presser, P.C.

(57) ABSTRACT

The present invention provides an electronic endoscope which enables the image pickup apparatus of the electronic endoscope to be easily replaced with image pickup apparatuses of different specifications. The electronic endoscope according to the present invention is configured by including a distal end member which is provided at a distal end portion of an insertion portion of the electronic endoscope, and which includes an image pickup apparatus mounting hole as a housing portion for housing an image pickup apparatus; and an outer shape adjusting member as an adjusting member which is provided between the image pickup apparatus and the image pickup apparatus mounting hole, and which fixes the image pickup apparatus in the image pickup apparatus mounting hole.

3 Claims, 13 Drawing Sheets

(56) References Cited

U.S. PATENT DOCUMENTS

| | | | |
|---|---|---|---|
| 4,773,396 A * | 9/1988 | Okazaki | 600/109 |
| 4,779,130 A * | 10/1988 | Yabe | 348/76 |
| 4,895,138 A * | 1/1990 | Yabe | 600/110 |
| 4,989,586 A * | 2/1991 | Furukawa | 600/110 |
| 4,993,405 A * | 2/1991 | Takamura et al. | 600/110 |
| 5,788,628 A * | 8/1998 | Matsuno et al. | 600/127 |
| 5,810,714 A * | 9/1998 | Takamura et al. | 600/134 |
| 5,894,369 A * | 4/1999 | Akiba et al. | 359/820 |
| 5,989,185 A * | 11/1999 | Miyazaki | 600/175 |
| 6,069,651 A * | 5/2000 | Tsuyuki et al. | 348/75 |
| 6,184,923 B1 * | 2/2001 | Miyazaki | 348/75 |
| 6,547,721 B1 * | 4/2003 | Higuma et al. | 600/133 |
| 6,767,322 B1 * | 7/2004 | Futatsugi et al. | 600/133 |
| 6,773,392 B2 * | 8/2004 | Kikuchi et al. | 600/109 |
| 6,796,939 B1 * | 9/2004 | Hirata et al. | 600/179 |
| 7,074,181 B2 * | 7/2006 | Futatsugi | 600/129 |
| 7,160,249 B2 * | 1/2007 | Hasegawa | 600/167 |
| 2002/0161284 A1 * | 10/2002 | Tanaka | 600/176 |
| 2004/0158159 A1 * | 8/2004 | Seto et al. | 600/476 |
| 2004/0190159 A1 * | 9/2004 | Hasegawa | 359/697 |
| 2007/0010711 A1 * | 1/2007 | Hasegawa | 600/168 |

\* cited by examiner

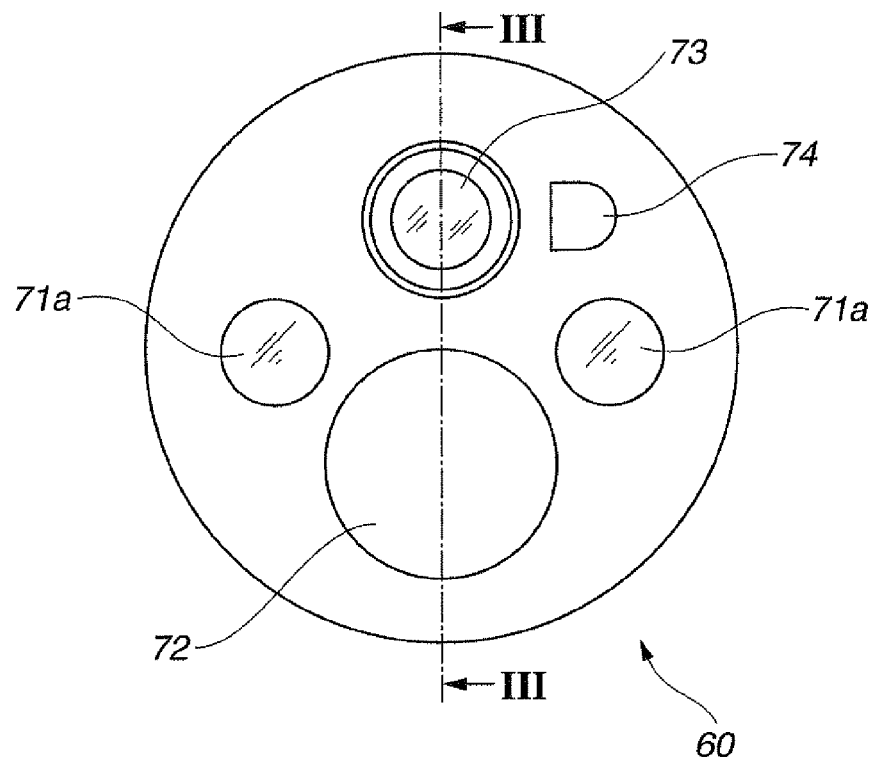
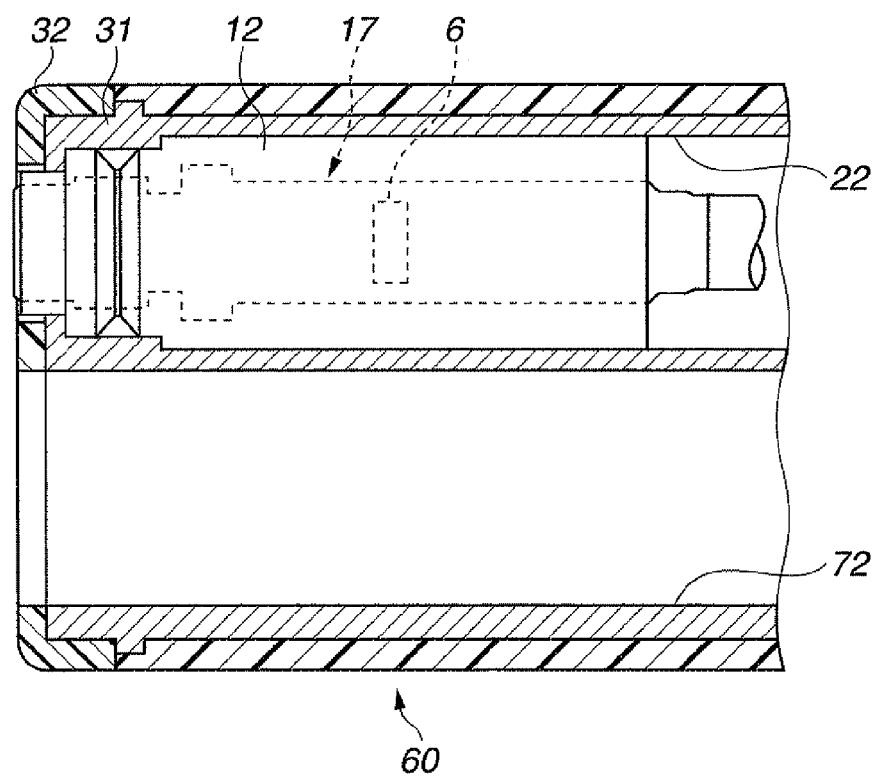

FIG.14
(a)
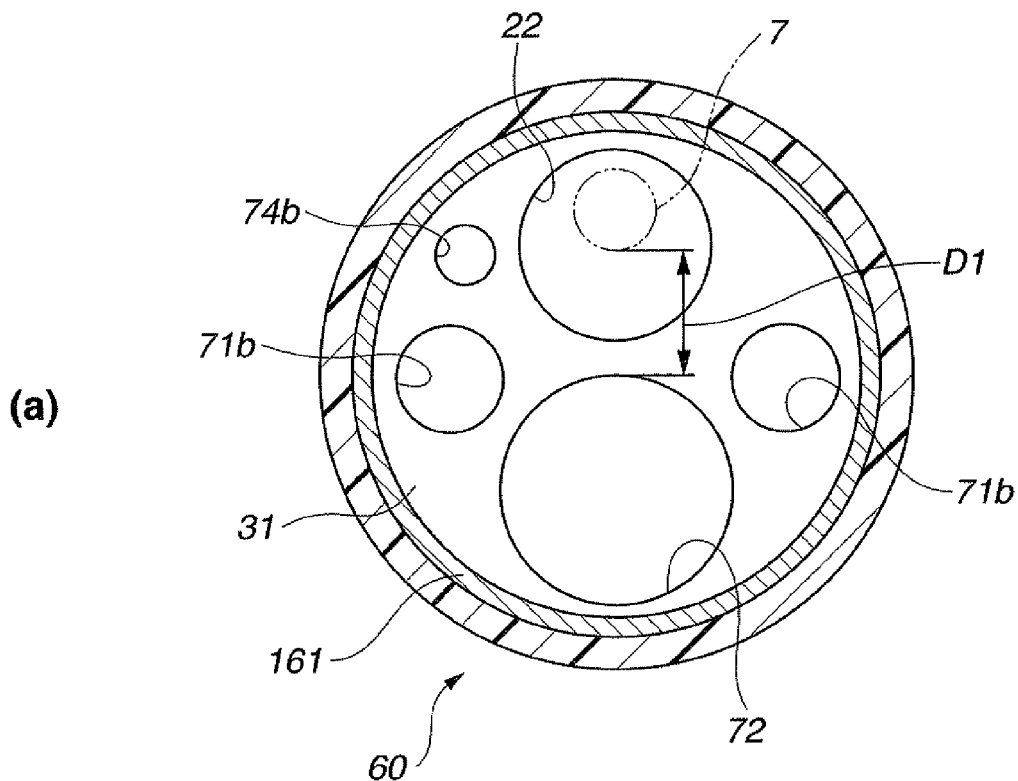
(b)
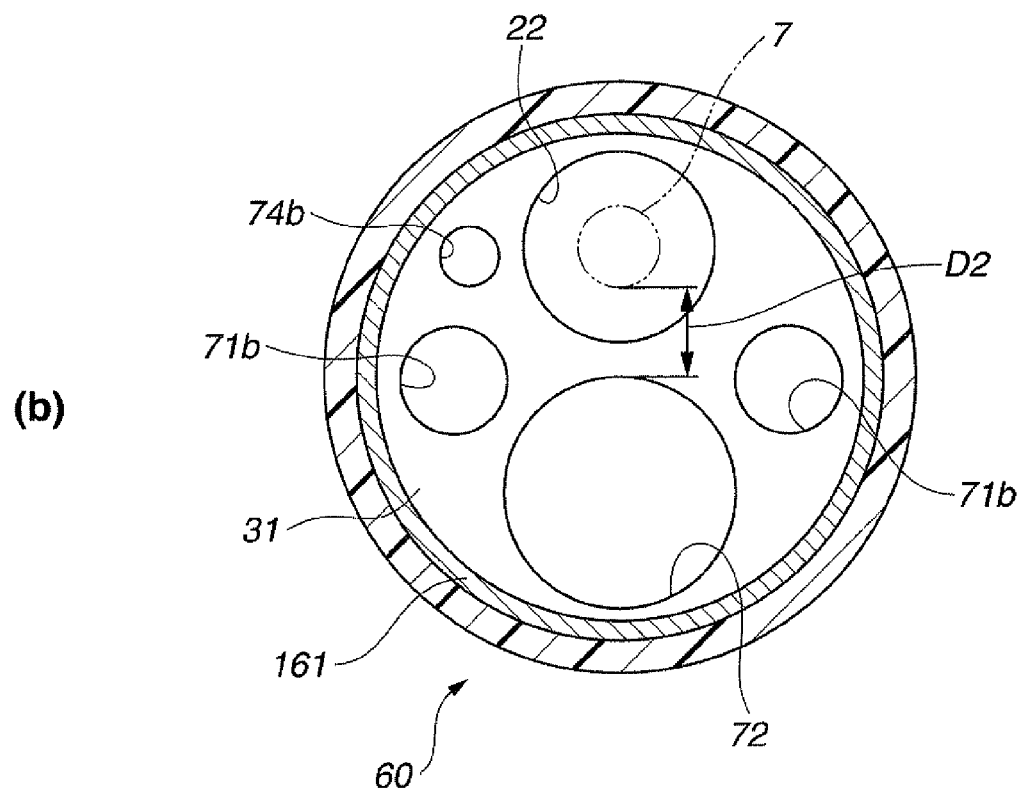

ELECTRONIC ENDOSCOPE

TECHNICAL FIELD

The present invention relates to an electronic endoscope, and more particularly to an electronic endoscope provided with an image pickup apparatus at a distal end of an insertion portion of the electronic endoscope.

BACKGROUND ART

In general, electronic endoscopes are configured by including a solid-state image pickup device, such as CCD, for imaging an observation object at a distal end of an insertion portion of the electronic endoscope, and are configured to output an image signal output from the solid-state image pickup device to a monitor or the like as an external device, and thereby making the image signal displayed as an observation image.

For example, in the endoscope disclosed in Japanese Patent Laid-Open No. 2000-14635, a circuit board for driving a solid-state image pickup device is connected to a distal end of a signal cable (signal line) for transmitting an image signal picked up by the solid-state image pickup device, behind the solid-state image pickup device at the distal end portion of the insertion portion of the endoscope. The solid-state image pickup device, the circuit board, and the distal end of the signal cable are arranged inside a shield frame which is a frame body for fixing these portions. Further, an objective optical system unit having an objective lens for forming an optical image of an object on the light receiving surface of the solid-state image pickup device is provided in front of the shield frame. In the following, a portion configured by combining the solid-state image pickup device, the circuit board, the signal cable, the shield frame, and the objective optical system unit is referred to as an image pickup apparatus for the sake of convenience.

The image pickup apparatus is fitted from behind into a stepped through hole provided in the distal end portion main body forming the distal end portion of the insertion portion, so as to be attached. Further, a V-shaped fixing groove is formed in the outer peripheral surface of the objective optical system unit. On the other hand, a fixing screw is arranged in a portion of the distal end main body, which portion faces the fixing groove. The fixing screw is screwed in the radial direction of the objective optical system unit, so as to abut against the fixing groove, whereby the distal end portion main body and the image pickup apparatus including the objective optical system unit are fixed to each other.

According to the technique disclosed in Japanese Patent Laid-Open No. 2000-14635, the stepped through hole provided in the distal end portion main body has a shape corresponding to the external shape of the image pickup apparatus. For this reason, the combination of the image pickup apparatus and the distal end portion main body is limited only to the case where they are in one to one correspondence. In the electronic endoscope having such a configuration, it is impossible to replace the image pickup apparatus with, for example, another image pickup apparatus having a shape different from that of the original one and including a different number of pixels therefrom and a lens system of a viewing angle different therefrom. That is, when an endoscope user intends to use the electronic endoscope in combination with an image pickup apparatus of different specification, for example, with an image pickup apparatus having an external shape which is made smaller than the external shape of the originally provided image pickup apparatus because of a change in at least one of the solid-state image pickup device and the objective optical system unit, the endoscope user needs to separately purchase an electronic endoscope of different specification.

The present invention has been made in order to solve the above described problem. An object of the present invention is to provide an electronic endoscope capable of easily replacing the image pickup apparatus of the electronic endoscope with an image pickup apparatus of different specification.

DISCLOSURE OF INVENTION

Means for Solving the Problem

An electronic endoscope according to an aspect of the present invention is featured by including: a distal end member which is provided at the distal end portion of the insertion portion of the electronic endoscope, and in which a housing portion for housing an image pickup apparatus is formed; and an adjusting member which is provided between the housing portion of the distal end member and the image pickup apparatus, and which holds the image pickup apparatus and is fixed in the housing portion.

The image pickup apparatus of the electronic endoscope according to a further aspect of the present invention is featured by including: an objective lens unit for forming an image of light from an object; and an image pickup device unit having a solid-state image pickup device arranged at the image forming position of the objective lens unit, and featured in that the adjusting member holds at least one of the objective lens unit and the image pickup device unit in the housing portion.

The image pickup apparatus of the electronic endoscope according to another aspect of the present invention is featured by including: a signal line electrically connected to a circuit board of the image pickup device; and a signal line positioning member adapted to position the signal line with respect to the housing portion.

The adjusting member of the electronic endoscope according to a still further aspect of the present invention is featured by being configured by a plurality of members.

An endoscope according to yet another aspect of the present invention is featured by including: an image pickup apparatus housing member which is provided in the endoscope, and in which a housing portion for housing an image pickup apparatus adapted to acquire an image of an object is formed; and an adjusting member which is provided between the housing portion of the image pickup apparatus housing member and the image pickup apparatus, and which holds the image pickup apparatus and is fixed in the housing portion.

BRIEF DESCRIPTION OF THE DRAWINGS

FIG. 2 is a partially enlarged view showing a distal end configuration of the electronic endoscope;

FIG. 3 is a partial cross-sectional view showing a distal end configuration of an electronic endoscope according to an embodiment of the present invention;

FIG. 14 is a figure explaining the arrangement of built-in components, taken along line XIV-XIV in FIG. 13.

BEST MODE FOR CARRYING OUT THE INVENTION

First Embodiment

Figure 1:
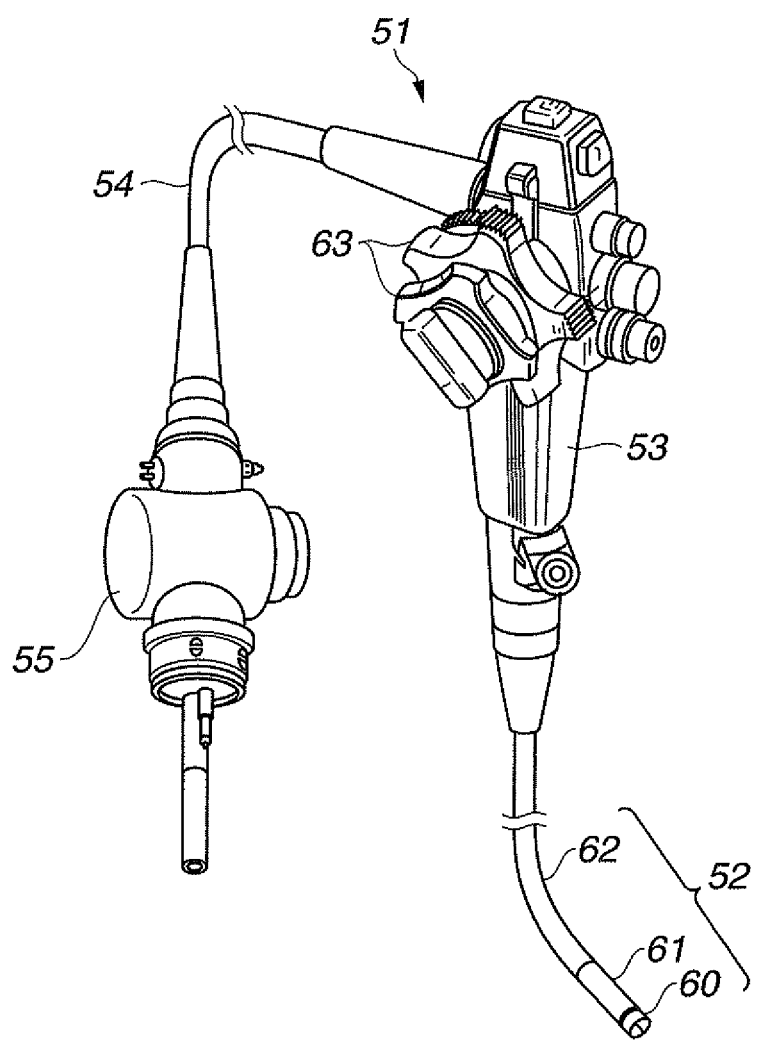
FIG. 1 is a view showing an entire configuration of an electronic endoscope.
Figure 4:
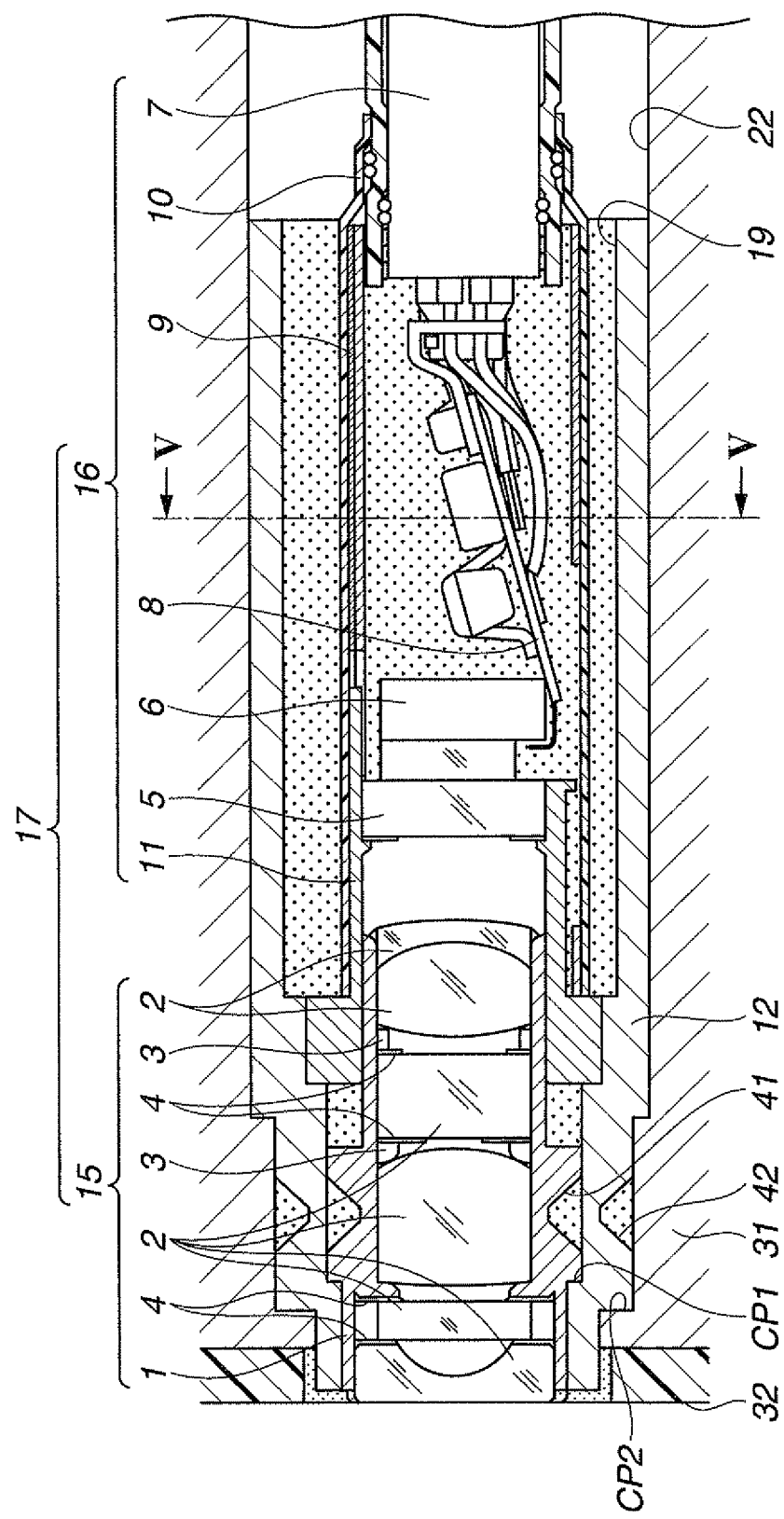
FIG. 4 is an enlarged partial sectional view showing a distal end configuration of an electronic endoscope according to a first embodiment of the present invention.
Figure 5:
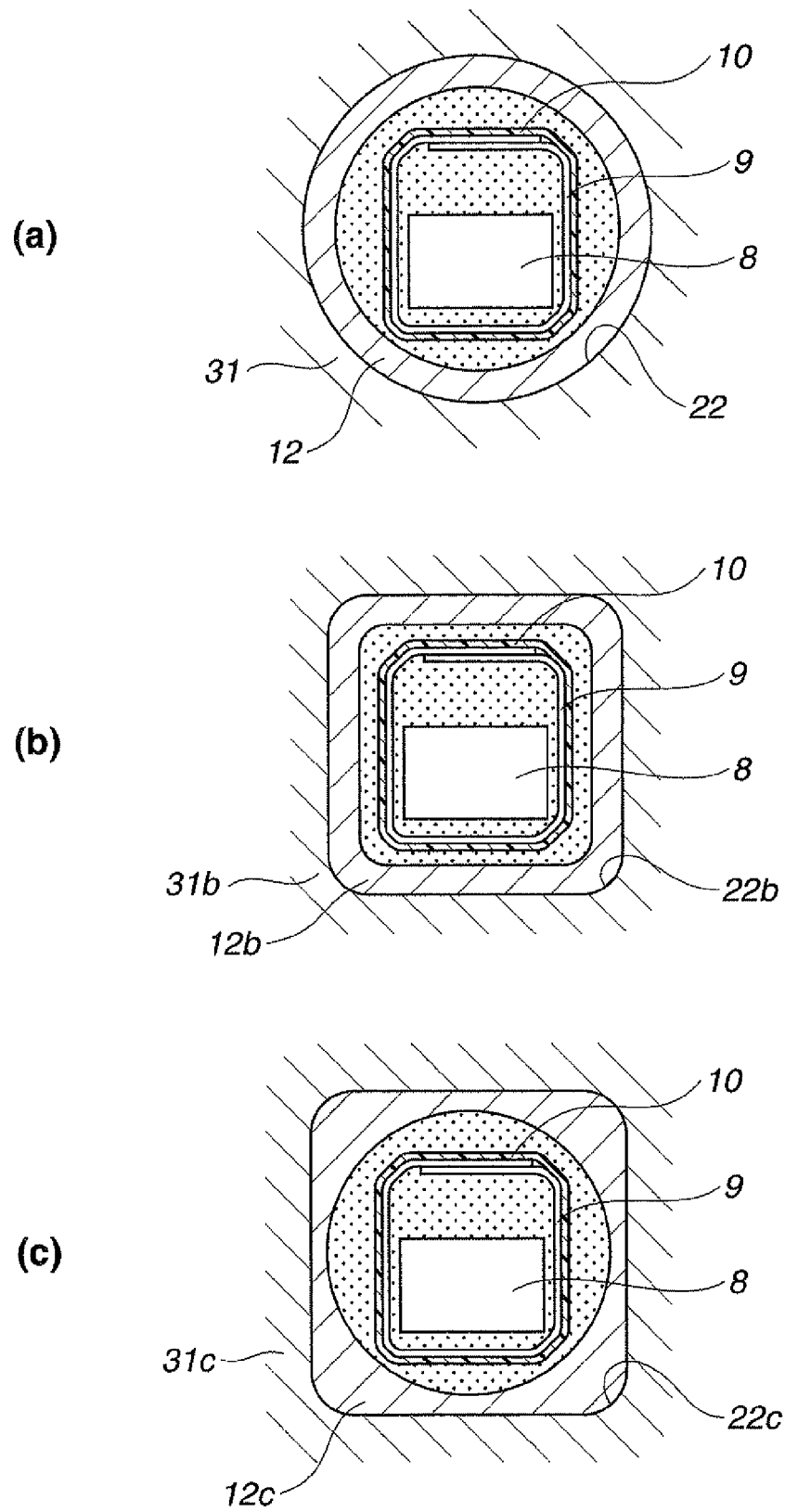
FIG. 5 is a cross-sectional view taken along line V-V in FIG. 4.
Figure 6:
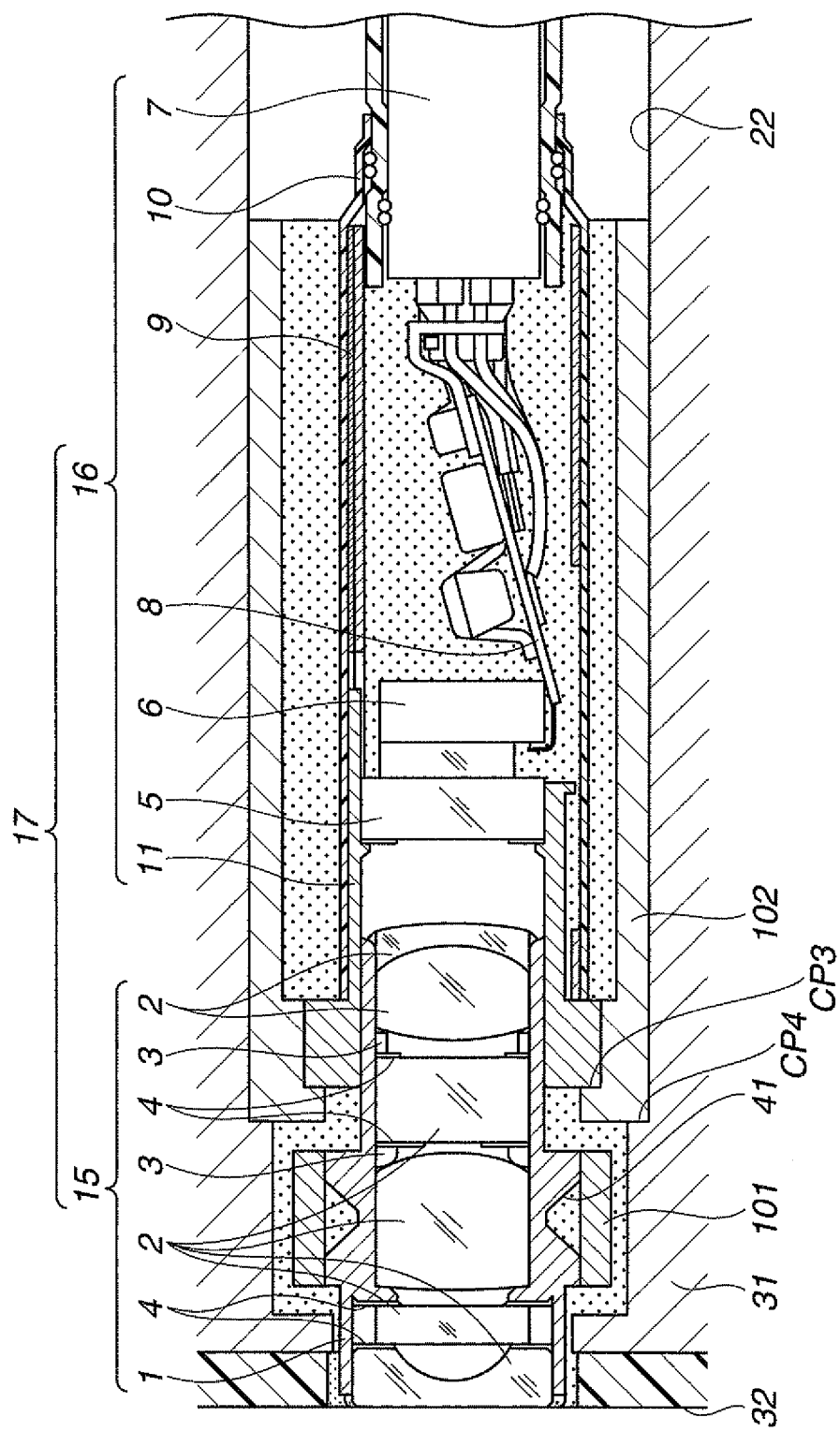
FIG. 6 is an enlarged partial sectional view showing a distal end configuration of an electronic endoscope according to a modification of the first embodiment of the present invention.

In the following, a first embodiment according to the present invention will be described with reference to the accompanying drawings. FIG. 1 is a view showing an entire configuration of an electronic endoscope. FIG. 2 is a partially enlarged view showing a distal end configuration of the electronic endoscope. FIG. 3 is a partial cross-sectional view showing a distal end configuration of an electronic endoscope according to an embodiment of the present invention. FIG. 4 is an enlarged partial sectional view showing a distal end configuration of an electronic endoscope according to a first embodiment of the present invention. FIG. 5 is a cross-sectional view taken along line V-V in FIG. 4. FIG. 6 is an enlarged partial sectional view showing a distal end configuration of an electronic endoscope according to a modification of the first embodiment of the present invention.

An electronic endoscope (endoscope) 51 according to the present embodiment shown in FIG. 1 is configured by including an operation portion 53 which is operated by being grasped by an operator, a thin and long insertion portion 52 which is formed at the distal end side of the operation portion 53 and is inserted into a body cavity, and a universal cord 54 extended from the side portion of the operation portion 53.

The insertion portion 52 is configured by including a rigid distal end portion 60 provided at the distal end of the insertion portion, a flexible bending portion 61 provided on the proximal end side of the distal end portion 60, and a long flexible tube portion 62 provided on the proximal end side of the bending portion 61. It is possible for the operator to bend the bending portion 61 by operating a bending operation lever 63 provided in the operation portion 53.

As shown in FIG. 2, on the distal end surface of the distal end portion 60, there are provided an observation window 73 of an image pickup apparatus 17 for imaging an object, two illumination windows 71a of a light guide adapted to emit illumination light for illuminating the object, and an opening portion of a forceps channel 72 for inserting treatment tools. Further, an air supply and water supply nozzle 74 for washing the surface of the observation window 73 is provided in the distal end surface of the distal end portion 60.

As shown in FIG. 4, the image pickup apparatus 17 is configured by including an objective lens unit 15 for forming an image of the object, and an image pickup device unit 16 incorporating a CCD 6 which is a solid-state image pickup device arranged at the image forming position behind the objective lens unit 15. Note that a CMOS image sensor or a known image sensor may be used instead of the CCD.

The electronic endoscope 51 is connected to an external light source apparatus and a video processor (both not shown) via a connector portion 55 provided in the proximal end of the universal cord 54. The illumination light generated by the light source apparatus is emitted from the illumination window 71a of the light guide, so as to illuminate the object. The image of the illuminated object is captured by the image pickup apparatus 17, and the image-pickup signal is sent to the video processor. The image-pickup signal is processed by the video processor, so as to be displayed as an endoscope observation image by a monitoring apparatus (not shown) connected to the video processor.

With reference to FIG. 3, there is described a configuration of the distal end portion 60 of the electronic endoscope 51. In the distal end portion 60, there is provided a rigid distal end member 31 for holding built-in components such as the image pickup apparatus 17, the light guide, and the forceps channel 72. The distal ends of the image pickup apparatus 17, the light guide, the forceps channel 72, and the like, are inserted into a plurality of through holes formed in the distal end member 31, respectively and fixed therein. The respective through holes configure housing portions of the image pickup apparatus 17, the light guide, the forceps channel 72, and the like. Further, the distal end portion of the distal end member 31 is covered with a distal end cover 32.

The image pickup apparatus 17 incorporating the CCD 6 is housed and fixed in an external shape adjusting member 12. The external shape adjusting member 12 is an adjusting member which is arranged in an image pickup apparatus mounting hole 22 as the housing portion, in order to hold the image pickup apparatus 17 and to adjust a clearance between the image pickup apparatus 17 and the distal end member 31. The external shape adjusting member 12 is inserted from the proximal end direction and fixed in the image pickup apparatus mounting hole 22 formed in the distal end member 31.

With reference to FIG. 4 and FIG. 5, there are described more details about a configuration of the image pickup apparatus 17 of the electronic endoscope 51 according to the present embodiment, and a method for fixing the image pickup apparatus 17 in the distal end member 31.

The image pickup apparatus 17 has portions whose outer peripheral shapes in a plane perpendicular to the central axis of the distal end portion 60 of the insertion portion 52 are substantially circular and substantially quadrangular, and is configured by including the objective lens unit 15 and the image pickup device unit 16 arranged in the proximal end of the objective lens unit 15. The objective lens unit 15 is configured by including an objective lens group 2 which is an optical system for forming an image of the object. The image pickup device unit 16 is configured by including the CCD 6 which is a solid-state image pickup device, a circuit board 8 which is electrically connected to the CCD 6, and on which electronic components for driving the CCD 6 are arranged, and a signal line 7 which is electrically connected to the circuit board 8 and extended in the proximal end direction. The signal-line 7 is used for power transmission and signal-transmission between the circuit board 8 and the video processor.

The object image formed by the objective lens unit 15 arranged at the distal end of the image pickup apparatus 17 is converted into an image-pickup signal by the image pickup device unit 16 having the CCD 6 arranged at the image forming position of the objective lens unit 15. The image-pickup signal is output to the video processor via the signal line 7 extended from the proximal end of the image pickup device unit 16.

The objective lens unit 15 has a configuration in which the objective lens group 2, spacers 3, and irises 4 are arranged in a through hole provided in the axial direction of an objective lens frame 1 which is a cylindrical exterior member. The respective optical devices, such as lenses, which configure the objective lens group 2, are arranged in the objective lens frame 1 in such a manner that intervals required for securing optical performance are maintained by inserting the spacers 3 and the irises 4 between the respective optical devices. The objective lens group 2, the spacers 3, and the irises 4 are fixed in the through hole of the objective lens frame 1 by fixing the lenses positioned at the both ends of the through hole to the objective lens frame 1 with an adhesive.

The objective lens frame 1 has a substantially cylindrical shape, whose outer shape is formed by three cylindrical portions which are arranged side by side along the axial direction and have different outer diameters. Among the three cylindrical portions configuring the external shape of the objective lens frame 1, the second cylindrical portion from the distal end has the largest outer diameter. The outer diameter of the cylindrical portions is reduced in the order of the distal end cylindrical portion to the proximal end cylindrical portion. For this reason, a stepped portion is formed in the proximal end of the distal end cylindrical portion. The axial positions of the external shape adjusting member 12 and the objective lens frame 1 are determined by making the stepped portion abut against an abutting portion CP1 of a stepped through hole 19, as will be described below, formed in the external shape adjusting member 12.

Further, a V-groove 41 having a V-shaped cross section is annularly formed in the outer peripheral surface of the cylindrical portion of the objective lens frame 1, which cylindrical portion is the second step from the distal end of the objective lens frame 1 and has the largest outer diameter. In the external shape adjusting member 12 as described below, a screw hole is formed in the radial direction in a position which faces the V-groove 41 of the objective lens frame 1 in the state where the objective lens frame 1 is housed in the stepped through hole 19. The objective lens frame 1 is fixed in the stepped through hole 19 of the external shape adjusting member 12 by such a way that a fixing screw is screwed into the screw hole to make the distal end of the fixing screw abut against the V-groove 41 of the objective lens frame 1. Note that a plurality of screw holes may be formed at different axial positions in the external shape adjusting member 12, to cope with the case where the axial position of the V-groove 41 is different for the image pickup apparatus to be used. Further, the objective lens frame 1 may also be fixed to the external shape adjusting member 12 by adhesion, without using the screw hole and the fixing screw.

In the cylindrical portion of the proximal end, the objective lens frame 1 is fitted into a through hole provided in a holding frame 11 of the image pickup device unit 16, as will be described below.

The outer peripheral portion of the image pickup device unit 16 is configured by two substantially cylindrical members of the holding frame 11 and a reinforcing frame 9 fitted into the proximal end of the holding frame 11. The signal line 7 is held at the proximal end of the reinforcing frame 9. The through hole is formed in the holding frame 11 arranged at the distal end of the image pickup device unit 16, and the proximal end side outer peripheral surface of the objective lens unit 15 is fitted into the distal end side inner peripheral surface of the through hole. Further, the outer peripheral surface of a cover glass 5 is fitted into the proximal end side inner peripheral surface of the through hole, and is fixed with an adhesive. A sealing glass is fixed on the light receiving surface of the CCD 6 with an UV curing type adhesive. The CCD 6 is fixed in the holding frame 11 by fixing the distal end side surface of the sealing glass to the proximal end side surface of the cover glass 5, using the UV curing type adhesive. That is, the objective lens unit 15 and the CCD 6 are positioned by the through hole formed in the holding frame 11. The circuit board 8 on which electronic components for driving the CCD 6 is arranged at the proximal end of the CCD 6 in the state where the surface of the circuit board is made to slightly incline with respect to the central axis of the image pickup device unit 16. The circuit board 8 is electrically connected to the CCD 6 via a lead wire. For reinforcing the CCD 6, the substantially cylindrical reinforcing frame 9 is arranged so as to cover the CCD 6 and the circuit board 8 connected thereto. The reinforcing frame 9 is fitted and fixed to the outer peripheral surface on the proximal end side of the holding frame 11. Further, the signal line 7 is connected to the circuit board 8 connected to the CCD 6, and is extended in the proximal end direction of the reinforcing frame 9. The holding frame 11, the reinforcing frame 9, and the distal end portion of the signal line 7 are covered with a heat shrinkable tube 10 for improving the durability. Further, the outer peripheral surface of the signal line 7 is covered with a tube for protecting the signal line 7.

The proximal end portion of the objective lens frame 1 in the objective lens unit 15 is inserted from the distal end side of the through hole in the holding frame 11 of the image pickup device unit 16, so as to be fitted in the through hole. Focus adjustment is performed by such a way that the objective lens unit 15 is moved in the axial direction so as to set the image forming position of the objective lens unit 15 at the light receiving surface of the CCD 6, and thereafter the objective lens unit 15 is fixed to the image pickup device unit 16 with an adhesive. Thereby, the image pickup apparatus 17 is formed.

The image pickup apparatus 17 configured as described above is inserted into the stepped through hole 19 formed in the external shape adjusting member 12 as will be described below, from the proximal end direction of the stepped through hole 19, so as to be fixed.

The external shape adjusting member 12 as an adjusting member includes a portion having a substantially circular outer peripheral shape in the plane perpendicular to the central axis of the distal end portion 60 of the insertion portion 52. Further, in the external shape adjusting member 12, there is formed the stepped through hole 19 in which the image pickup apparatus 17 is inserted in the central axis direction, so as to be fixed. The stepped through hole 19 has three stepped portions, in which the inner diameter of the distal end stepped portion is the smallest, and the inner diameter of the proximal end stepped portion is the largest. That is, the inner diameter of the stepped through hole 19 becomes larger in steps from the distal end side to the proximal end side.

The positions of the image pickup apparatus 17 and the external shape adjusting member 12 in the axial direction are determined by such a way that the proximal end direction facing surface of the most distal end side stepped portion of the stepped through hole 19 is set as the abutting portion CP1, and that the stepped portion provided in the objective lens frame 1 of the image pickup apparatus 17 is made to abut against the abutting portion CP1.

Further, the positions of the image pickup apparatus 17 and the external shape adjusting member 12 in the direction perpendicular to the axis, that is, in the radial direction are determined by using, as fitting portions, the cylindrical portion having the outer diameter as the second step from the distal end of the objective lens frame 1 of the image pickup apparatus 17, and the hole portion having the inner diameter as the second step from the distal end of the stepped through hole 19.

The dimensions which do not contribute to the mutual fitting and positioning of the stepped through hole 19 and the image pickup apparatus 17 are set so as to secure a suitable clearance for avoiding the double fitting and the double positioning and for improving the durability.

The external shape of the external shape adjusting member 12 has three cylindrical portions which are arranged side by side along the axial direction and have different outer diameters. The three cylindrical portions configuring the external shape of the external shape adjusting member 12 are configured so that the outer diameter of the distal end cylindrical portion is the smallest, the outer diameter of the second cylindrical portion is the second largest, and the outer diameter of the proximal end cylindrical portion is the largest. For this reason, two stepped portions are formed on the external shape of the external shape adjusting member 12.

In the distal end member 31, there is provided the image pickup apparatus mounting hole 22 as a housing portion in which the external shape adjusting member 12 is inserted and fixed. The image pickup apparatus mounting hole 22 has two stepped portions, in which the inner diameter of the distal end stepped portion is the smallest, and the inner diameter of the proximal end stepped portion is the largest. That is, the inner diameter of the image pickup apparatus mounting hole 22 is increased in steps from the distal end side to the proximal end side. The positions of the external shape adjusting member 12 and the distal end member 31 in the axial direction are determined by such a way that the proximal end direction facing surface of the most distal end side stepped portion of the image pickup apparatus mounting hole 22 is set as an abutting portion CP2, and that the most distal end side stepped portion provided in the external shape adjusting member 12 is made to abut against the abutting portion CP2.

Further, the positions of the external shape adjusting member 12 and the distal end member 31 in the direction perpendicular to the axis of the members, that is, in the radial direction are determined by using, as fitting portions, the cylindrical portion having the outer diameter as the second step from the distal end of the external shape adjusting member 12, and the hole portion having the inner diameter as the second step from the distal end of the image pickup apparatus mounting hole 22.

Here, the dimensions which do not contribute to the mutual fitting and positioning of the image pickup apparatus mounting hole 22 and the external shape adjusting member 12, are set so as to secure a suitable clearance for avoiding the double fitting and the double positioning and for improving the durability.

Further, a V-groove 42 having a V-shaped cross section is annularly formed in the outer peripheral surface of the cylindrical portion having the outer diameter as the second step from the distal end. Further, in the distal end member 31, a screw hole is formed in the radial direction in a position which faces the V-groove 42 when the stepped portion of the external shape adjusting member 12 is inserted until the stepped portion abuts against the abutting portion CP2 of the image pickup apparatus mounting hole 22 of the distal end member 31. The external shape adjusting member 12 is fixed in the image pickup apparatus mounting hole 22 of the distal end member 31 by such a way that a fixing screw is screwed into the screw hole to make the distal end of the fixing screw abut against the V-groove 42. Note that a plurality of screw holes may be formed at different axial positions in the distal end member 31, for the case where the position in the axial direction of the V-groove 41 is changed due to the shape of the external shape adjusting member 12 to be used.

It is preferred that the distal end surface of the external shape adjusting member 12 is positioned on the substantially same plane as the distal end surface of the objective lens frame 1, in consideration of the workability at the time of providing repair adhesion to the clearance between the distal end cover 32 and the external shape adjusting member 12.

A groove for attaching an O ring for securing the water tightness may be provided in the outer peripheral surface of the external shape adjusting member 12.

With the above described configuration, the image pickup apparatus 17 having an outer peripheral shape smaller than the inner peripheral shape of the image pickup apparatus mounting hole 22 provided in the distal end member 31 can be positioned and fixed in the image pickup apparatus mounting hole 22. Therefore, it is possible to replace the originally provided image pickup apparatus with an image pickup apparatus of different specification, in the electronic endoscope in which conventionally, the originally provided image pickup apparatus cannot be replaced with the image pickup apparatus of different specification because the external shape of the image pickup apparatus of different specification does not match the shape of the image pickup apparatus mounting hole. For example, as shown in FIG. 5b and FIG. 5c, when the inner peripheral shape of the image pickup apparatus mounting holes 22b and 22c respectively formed in the distal end member 31b and the distal end member 31c is substantially quadrangular, it is possible to position and fix the image pickup apparatus 17 by using external shape adjusting members 12b and 12c having an outer peripheral shape fittable to the image pickup apparatus mounting holes 22b and 22c.

Note that in the above described first embodiment, the outer diameter of the second step from the distal end of the objective lens frame 1 and the abutting portion CP1 of the stepped through hole 19 are used as portions where the stepped through hole 19 and the image pickup apparatus 17 are mutually fitted and made to abut against each other, but the fitting and abutting may also be effected in another portions, respectively. For example, it may also be configured so that the stepped through hole 19 and the image pickup apparatus 17 are mutually fitted and made to abut against each other by respectively using the outer diameter portion of the holding frame 11 and the stepped portion of the second step from the distal end of the stepped through hole 19.

Further, the cylindrical portion having the diameter as the second step from the distal end, and the stepped portion provided in the most distal end side are used as the portions where the image pickup apparatus mounting hole 22 and the external shape adjusting member 12 are mutually fitted and made to abut against each other, but these may also be fitted and made to abut against each other in another portions, respectively. For example, it may also be configured such that the image pickup apparatus mounting hole 22 and the external shape adjusting member 12 are mutually fitted and made to abut against each other by respectively using the cylindrical portion having the diameter as the third step from the distal end, and the stepped portion as the second step from the distal end.

Further, in the above described first embodiment, the external shape adjusting member 12 is configured by one member and provided so as to cover the entire outer peripheral portion of the image pickup apparatus 17. However, the external shape adjusting member 12 may be configured to be divided into a plurality of members in the axial direction, so that the plurality of members function similarly to the case where the external shape adjusting member 12 is configured by one member.

For example, as shown in FIG. 6, it may also be configured so that the outer peripheral portion of the objective lens unit 15, and the outer peripheral portion of the image pickup device unit 16 are covered by different members from each other. Here, an objective lens frame external shape adjusting member 101 and an image pickup device unit external shape adjusting member 102 are fixed to the outer peripheral portions of the objective lens unit 15 and the image pickup device unit 16 of the image pickup apparatus 17, respectively.

In the image pickup device unit external shape adjusting member 102 which has a substantially cylindrical shape, there is formed a through hole provided with an abutting portion CP3 as a stepped portion which is made to axially abut against the distal end of the image pickup device unit 16 of the image pickup apparatus 17. Further, the through hole of the image pickup device unit external shape adjusting member 102 has an inner peripheral surface which can be fitted with the outer peripheral surface of the distal end portion of the image pickup device unit 16, here the outer peripheral surface of the distal end portion of the holding frame 11. The image pickup apparatus 17 is positioned and fixed in the image pickup device unit external shape adjusting member 102 by such a way that the image pickup device unit 16 is inserted into the through hole of the image pickup device unit external shape adjusting member 102 from the proximal end direction to the position where the image pickup device unit 16 abuts against the abutting portion CP3, so as to be fitted.

Further, the image pickup device unit external shape adjusting member 102 has an outer diameter adapted to fit in a hole having an inner diameter as the third step from the distal end of the image pickup apparatus mounting hole 22. The distal end surface of the image pickup device unit outer shape adjusting member 102 is made to abut against an abutting portion CP4 which is the proximal end facing surface of the second stepped portion from the distal end of the image pickup apparatus mounting hole 22, so as to be fixed in the image pickup apparatus mounting hole 22 with an adhesive. Thereby, the image pickup apparatus 17 and the image pickup apparatus mounting hole 22 are positioned and fixed.

Further, the cylindrical objective lens frame external shape adjusting member 101 is externally fitted with the outer peripheral surface of the cylindrical portion having the largest outer diameter as the second step from the distal end of the objective lens frame 1 in the objective lens unit 15, so as to be fixed. The outer diameter of the objective lens frame external shape adjusting member 101 is set so as to suitably form a clearance with the image pickup apparatus mounting hole 22. The clearance makes it possible to optimize the amount of the adhesive to be filled, and thereby fixing the image pickup apparatus 17 to the distal end member 31. Generally, adhesive is reduced in volume when cured. For this reason, when the clearance between the image pickup apparatus 17 and the image pickup apparatus mounting hole 22 is large, and when the used amount of the adhesive filled in the clearance is large, a space may be formed between the image pickup apparatus 17 and the image pickup apparatus mounting hole 22 after the adhesive is cured. When the space is formed between the image pickup apparatus 17 and the image pickup apparatus mounting hole 22, moisture may easily enter through the space, so as to affect the durability of the image pickup apparatus 17. However, as in the present embodiment it is possible to reduce the amount of the adhesive to be used by providing the rigid objective lens frame external shape adjusting member 101 between the image pickup apparatus 17 and the image pickup apparatus mounting hole 22. This makes it possible to reduce the volume amount of the adhesive which is to be reduced when the adhesive is cured, and hence it is possible to prevent the formation of the space between the image pickup apparatus 17 and the image pickup apparatus mounting hole 22. Therefore, according to the present embodiment, the infiltration of moisture can be suppressed, so that it is possible to minimize the influence of moisture on the durability of the image pickup apparatus 17.

In the above described configuration shown in FIG. 6, the image pickup apparatus 17 and the image pickup apparatus mounting hole 22 are positioned and fixed via the image pickup device unit external shape adjusting member 102. For this reason, the objective lens frame external shape adjusting member 101 does not contribute to position the image pickup apparatus 17. Thus, in the case where no fixing problem arises even though the objective lens frame external shape adjusting member 101 is not attached, the objective lens frame external shape adjusting member 101 need not be attached and may be selectively attached in dependence upon the shape of the objective lens frame 1 of the image pickup apparatus 17 to be used.

Second Embodiment

Figure 7:
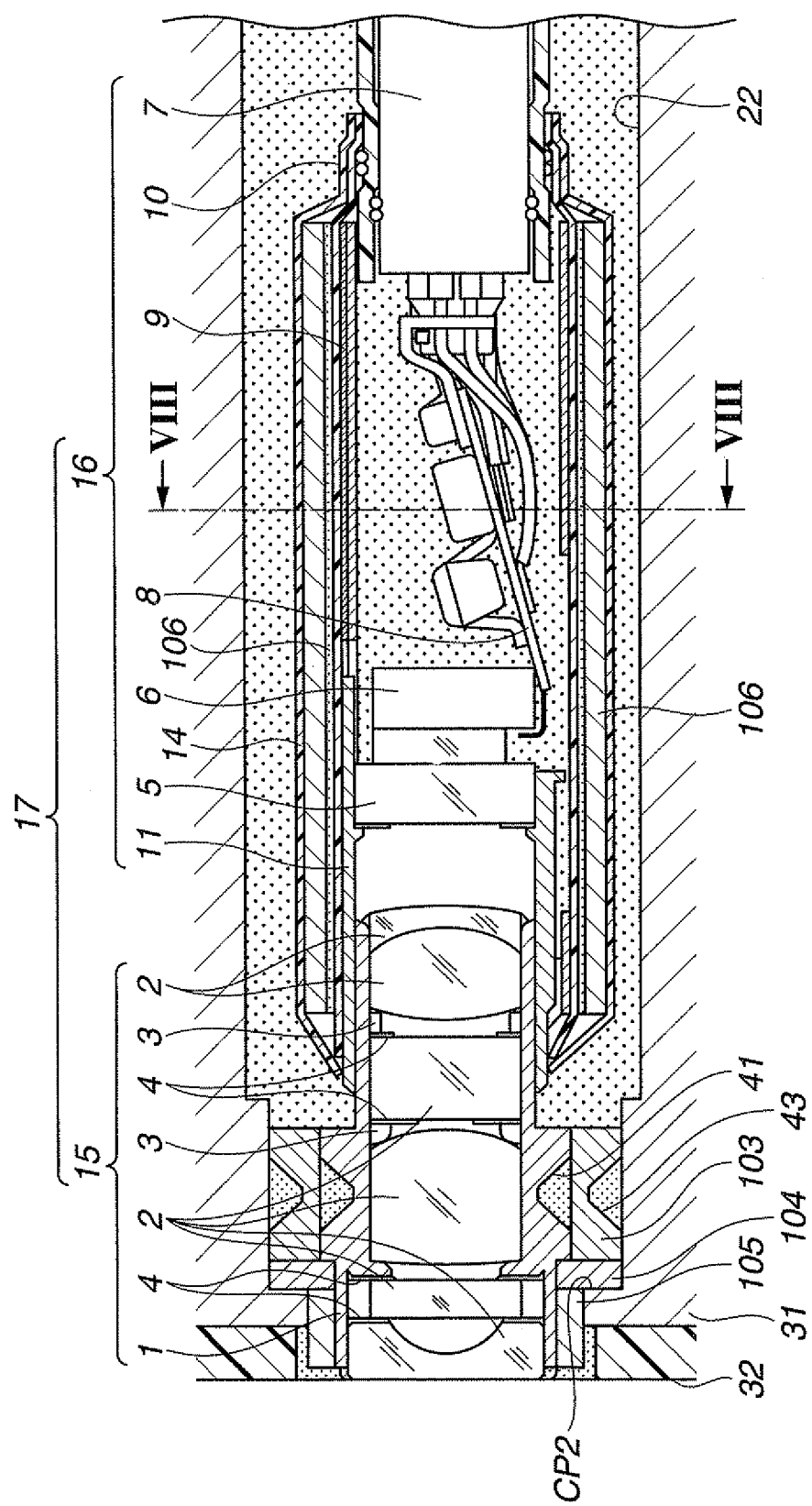
FIG. 7 is an enlarged partial sectional view showing a distal end configuration of an electronic endoscope according to a second embodiment of the present invention.
Figure 8:
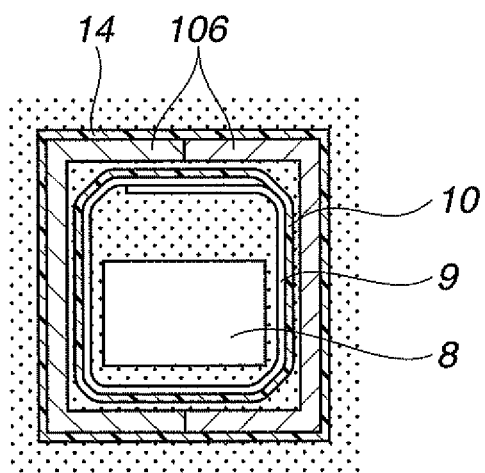
FIG. 8 a cross-sectional view taken along line VIII-VIII in FIG. 7.
Figure 9:
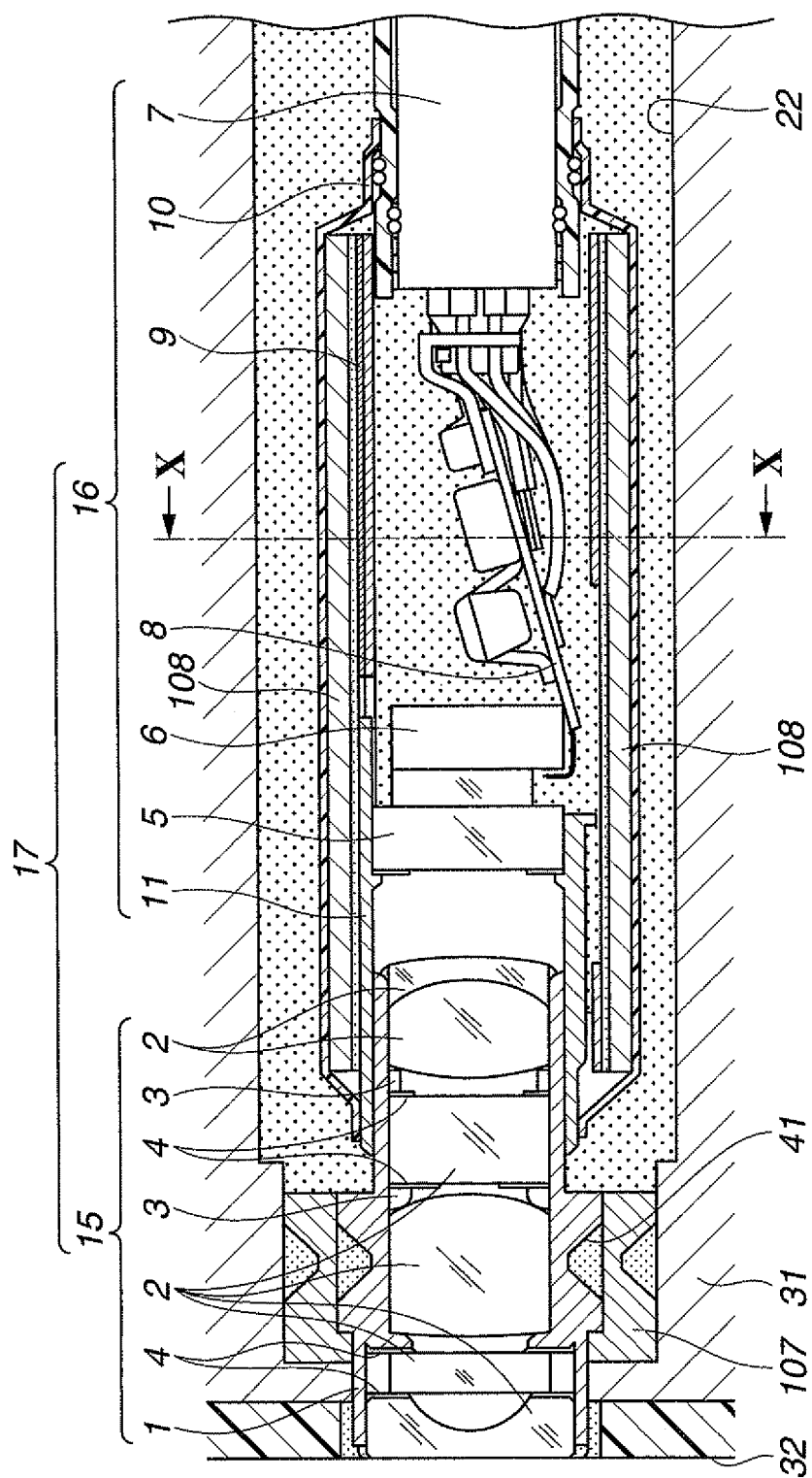
FIG. 9 is an enlarged partial sectional view showing a distal end configuration of an electronic endoscope according to a modification of the second embodiment of the present invention.
Figure 10:
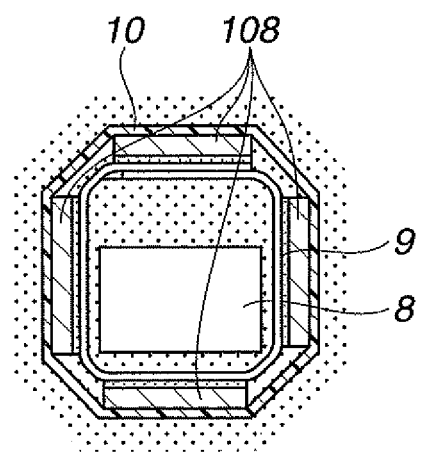
FIG. 10 is a cross-sectional view taken along line X-X in FIG. 9.
Figure 11:
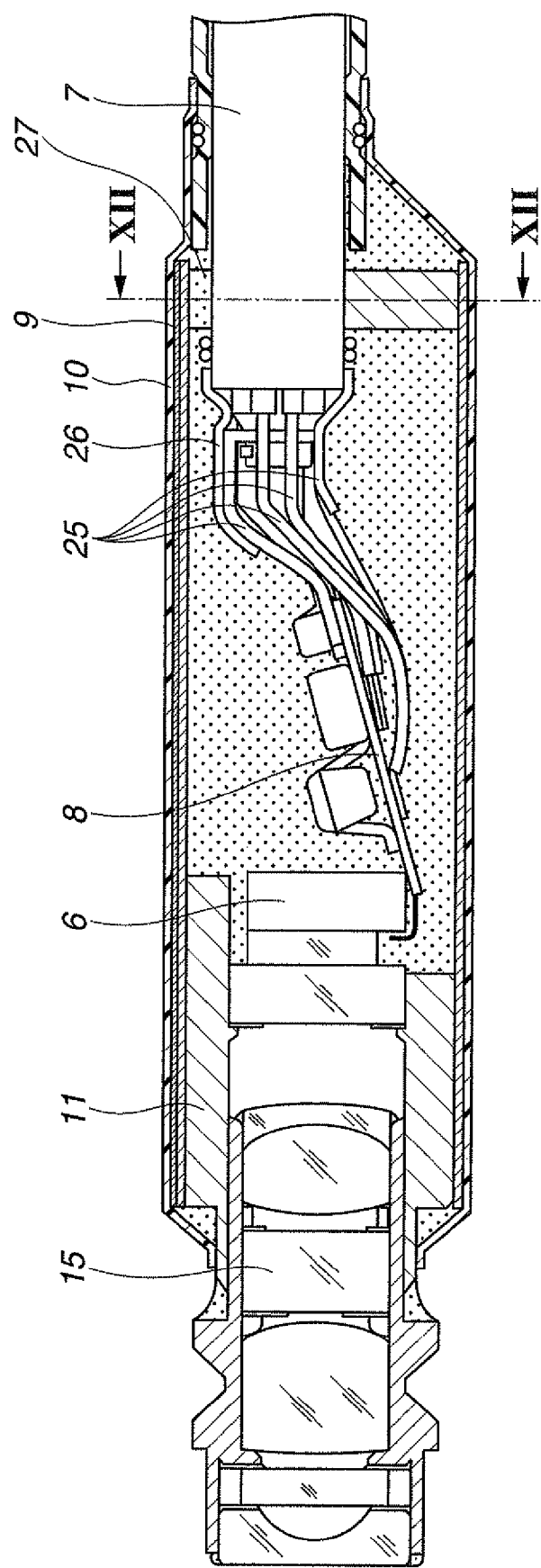
FIG. 11 is a sectional view explaining a method for regulating an extending position of a signal line.
Figure 12:
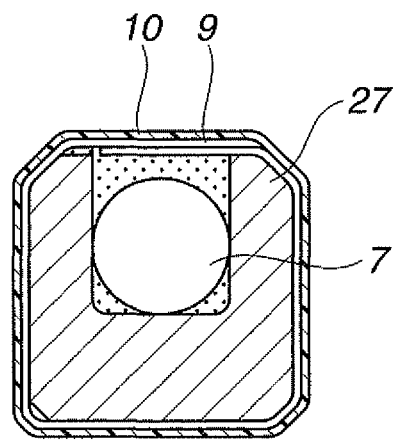
FIG. 12 is a cross-sectional view taken along line XII-XII in FIG. 11.

In the following, a second embodiment according to the present invention will be described with reference to the accompanying drawings. FIG. 7 is an enlarged partial sectional view showing a distal end configuration of an electronic endoscope according to a second embodiment of the present invention. FIG. 8 is a cross-sectional view taken along line VIII-VIII in FIG. 7. FIG. 9 is an enlarged partial sectional view showing a distal end configuration of an electronic endoscope according to a modification of the second embodiment of the present invention. FIG. 10 is a cross-sectional view taken along line X-X in FIG. 9. FIG. 11 is a sectional view explaining a method for regulating an extending position of a signal line. FIG. 12 is a cross-sectional view taken along line XII-XII in FIG. 11.

In the above described first embodiment according to the present invention, the external shape adjusting member 12 as an adjusting member is configured so as to make the entire periphery of the outer peripheral surface of the image pickup apparatus 17 covered by one continuous member, but the external shape adjusting member 12 may be configured by a plurality of members divided in the axial direction and the peripheral direction of the distal end portion 60 of the insertion portion 52. An example of a configuration as the second embodiment according to the present invention will be described with reference to FIG. 7 and FIG. 8. Note that in the following description, components common to the first embodiment are denoted by the same reference numerals and characters, and their description is suitably omitted.

A fitting portion shape adjusting member 103 having a hollow cylindrical shape is fixed so as to cover the outer peripheral surface of the cylindrical portion having the largest outer diameter as the second step from the distal end of the objective lens frame 1 of the image pickup apparatus 17. The fitting portion shape adjusting member 103 has an outer diameter adapted to fit in the hole having the inner diameter as the second step from the distal end of the image pickup apparatus mounting hole 22.

Further, a V-groove 43 having a V-shaped cross section is annularly formed on the outer peripheral surface of the fitting portion shape adjusting member 103. Further, in the distal end member 31, a screw hole is formed in the radial direction at a position, which faces the V-groove 43 when the fitting portion shape adjusting member 103 having the V-groove 43 is inserted in the image pickup apparatus mounting hole 22. The fitting portion shape adjusting member 103 is fixed in the image pickup apparatus mounting hole 22 of the distal end member 31 by screwing a fixing screw into the screw hole, and making the distal end of the fixing screw abut against the V-groove. Here, a groove for attaching an O ring for securing the water tightness may also be provided in the outer peripheral surface of the fitting portion shape adjusting member 103.

In order to adjust the axial distance between the abutting portion CP2 which is the proximal end direction facing surface of the most distal end side stepped portion of the image pickup apparatus mounting hole 22, and the most distal end side stepped portion of the objective lens frame 1, a hollow cylindrical abutting position adjusting member 104 is provided so as to cover the outer peripheral surface of the cylindrical portion at most distal end of the objective lens frame 1. The abutting position adjusting member 104 has a shape which comes into contact with the stepped portion at the most distal end of the objective lens frame 1 and with the abutting portion CP2 of the image pickup apparatus mounting hole 22 when the image pickup apparatus 17 is inserted into the image pickup apparatus mounting hole 22. Also, the abutting position adjusting member 104 is externally fitted and fixed to the cylindrical portion as the distal end of the objective lens frame 1.

Further, a projecting portion shape adjusting member 105 having a hollow cylindrical shape is arranged on the distal end side of the abutting position adjusting member 104 so as to cover the outer peripheral surface of the cylindrical portion which is the most distal end of the objective lens frame 1. The projecting portion shape adjusting member 105 has an external shape for optimizing the clearance between the image pickup apparatus 17 and the image pickup apparatus mounting hole 22. Thus, the clearance makes it possible to optimize the amount of the adhesive to be filled, so that the image pickup apparatus 17 can be fixed to the distal end member 31.

The image pickup apparatus 17 is positioned and fixed to the image pickup apparatus mounting hole 22 by such a way that in the state where the fitting portion shape adjusting member 103, the abutting position adjusting member 104, and the projecting portion shape adjusting member 105 are fixed, the image pickup apparatus 17 is inserted into the image pickup apparatus mounting hole 22 from the proximal end direction to be abutted. At this time, it is preferred that the distal end surface of the projecting portion shape adjusting member 105 is positioned on the substantially same plane as the distal end surface of the objective lens frame 1, in consideration of the workability of being mended and adhered to the space between the distal end cover 32 and the projecting portion shape adjusting member 105.

Further, on the outer peripheral surface of a heat shrinkable tube 10 adapted to cover the outer peripheral surface of the image pickup device unit 16 of the image pickup apparatus 17, there is fixed an image pickup device unit external shape adjusting member 106 for adjusting a clearance between the external shape of the image pickup device unit 16 and the image pickup apparatus mounting hole 22. The image pickup device unit external shape adjusting member 106 has a U-shaped cross sectional shape. Further, when two of the same image pickup device unit external shape adjusting members are used and the recessed portions of the members are made to face each other, the members are formed into a shape capable of covering the entire outer peripheral surface of the image pickup device unit 16. The image pickup device unit external shape adjusting member 106 is fixed to the outer peripheral surface of the heat shrinkable tube 10 with an adhesive or the like. The outer peripheral surface of the image pickup device unit external shape adjusting member 106 is covered with a reinforcing heat shrinkable tube 14. Thus, by narrowing the clearance, it is possible to optimize the amount of the adhesive to be filled in the clearance, and thereby fixing the image pickup apparatus 17 to the distal end member 31.

With the above described configuration, the image pickup apparatus 17 having an outer diameter smaller than the inner diameter of the image pickup apparatus mounting hole 22 provided in the distal end member 31, can be positioned and fixed to the image pickup apparatus mounting hole 22. Therefore, the replacement of the image pickup apparatus can be effected in the electronic endoscope whose original image pickup apparatus cannot be conventionally replaced with an image pickup apparatus of different specification because the shape of the image pickup apparatus mounting hole does not match the external shape of the image pickup apparatus of different specification.

Note that the reinforcing heat shrinkable tube 14 may be eliminated when sufficient fixing strength between the image pickup device unit external shape adjusting member 106 and the heat shrinkable tube 10 can be obtained only by fixation with an adhesive or the like.

Further, the image pickup device unit external shape adjusting member 106 is not a member used for the fitting and positioning between the image pickup apparatus 17 and the image pickup apparatus mounting hole 22. Thus, the image pickup device unit external shape adjusting member 106 need not be attached, in the case where no problem arises even though the member is not attached. Whether or not to attach the image pickup device unit external shape adjusting member 106 may be selected in dependence upon the shape of the image pickup device unit 16 of the image pickup apparatus 17 to be used.

In the above described configuration according to the second embodiment of the present invention, the three members of the fitting portion shape adjusting member 103, the abutting position adjusting member 104 and the projecting portion shape adjusting member 105 are used for positioning and fixing the objective lens frame 1 to the image pickup apparatus mounting hole 22. However, only one of the three members may be used as required, or among three members, the two or more members may be integrally formed. For example, when only one member is used, the member may have a function to position the image pickup device unit 16 with respect to the image pickup apparatus mounting hole 22 in the insertion axis direction and the radial direction. As shown in FIG. 9, the member may also be configured so that the fitting portion shape adjusting member 103 is integrally formed with the abutting position adjusting member 104. The configuration makes it possible to simplify the assembling work.

Further, in the above described configuration according to the second embodiment of the present invention, the image pickup device unit external shape adjusting member 106 has the shape adapted to cover the entire outer peripheral surface of the image pickup device unit 16 in order to adjust the clearance between the external shape of the image pickup device unit 16 and the image pickup apparatus mounting hole 22. However, the image pickup device unit external shape adjusting member 106 may have a shape so as to be attached to at least a part of the outer peripheral surface of the image pickup device unit 16. For example, as shown in FIG. 9 and FIG. 10, it may be configured so that one flat plate-shaped image pickup device unit external shape adjusting member 108 is arranged for each surface of the image pickup device unit 16 having a rectangular cross section. In this case, the merely flat plate-shaped image pickup device unit external shape adjusting member 108 is only arranged, and hence the clearance can be adjusted at low cost. Further, it is possible to easily change the shape of the image pickup device unit external shape adjusting member 108, and hence it is possible to easily deal with external shapes of various image pickup device units 16.

In the image pickup apparatus 17 according to the embodiment of the present invention shown in FIG. 9 and FIG. 10, the image pickup device unit external shape adjusting member 108 is fixed to the outer peripheral surface of the reinforcing frame 9 with an adhesive or the like. It is configured so that the outer peripheral surface of the image pickup device unit external shape adjusting member 108 is covered with the heat shrinkable tube 10. In the configuration according to the second embodiment of the present invention, it is configured such that the image pickup device unit external shape adjusting member 106 is fixed to the outer peripheral surface of the heat shrinkable tube 10, and further, the outer peripheral surface is covered with the reinforcing heat shrinkable tube 14. However, according to the present configuration shown in FIG. 9 and FIG. 10, the heat shrinkable tube for covering the outer peripheral surface of the image pickup device unit 16 can be reduced to one layer, which makes it possible to simplify the assembling work.

Meanwhile, in the image pickup apparatus 17 of the electronic endoscope according to the embodiment of the present invention, it is possible that the extending position of the signal line 7 extended from the proximal end of the image pickup device unit 16 is not made substantially coincident with the central axis of the objective lens unit 15, but is arbitrarily positioned in the range where the extending position can be included inside the reinforcing frame 9. In the following, the positioning method of the signal line 7 extended from the image pickup device unit 16 will be described with reference to FIG. 11 and FIG. 12. FIG. 11 is a sectional view explaining a method for regulating the extending position of the signal line. FIG. 12 is a cross-sectional view taken along line XII-XII in FIG. 11.

In the inside of the image pickup device unit 16, in order to improve wiring at the time of soldering each core wire of the signal line 7 to the circuit board 8, a cable strip portion 25 is provided at the distal end of the signal line 7. The cable strip portion 25 is set to be longer as compared with the case where the extending position of the signal line 7 is made substantially coincident with the central axis of the objective lens unit 15, in order to provide spatial allowance for positioning the extending position. Further, the periphery of the cable strip portion 25 is covered with a cable strip portion heat shrinkable tube 26 to regulate the external shape of the cable strip portion, so as to prevent a size of the external shape of the cable strip portion 25 from becoming too large.

A plate-shaped signal line positioning member 27 is fitted in the opening portion of the reinforcing frame 9 in the form of closing the opening portion of the proximal end of the reinforcing frame 9. The signal line positioning member 27 has an opening portion for positioning and fixing the extending position of the signal line 7 in the inside of the reinforcing frame 9. The opening portion of the signal line positioning member 27 is formed to pass through in the central axial direction of the objective lens unit 15. Further, the opening portion is connected to the outer periphery of the signal line positioning member 27, when viewed from the central axial direction of the objective lens unit 15. That is, the opening portion is formed as an U-shaped notch in the signal line positioning member 27. The extending position of the signal line 7 is regulated in the inside of the reinforcing frame 9 by inserting the signal line 7 into the opening portion of the signal line positioning member 27 and assembling the image pickup device unit 16.

With the above described configuration, the extending position of the signal line 7 extended from the proximal end of the image pickup device unit 16, can be positioned in an arbitrary position in the range where the extending position can be included inside of the reinforcing frame 9 without difficulty in the state where the external shape of the cable strip portion 25 is regulated.

In the replacement with a different image pickup apparatus, there may be a case where the image pickup apparatus cannot be housed in the housing portion not only because of the difference in the image pickup device unit and the objective lens unit but also because of the difference in the extending position of the signal line. However, according to the present embodiment, the extending position of the signal line 7 can be positioned at a suitable position by the signal line positioning member 27, and hence it is possible to arrange the image pickup apparatus 17 in the distal end member 31.

Figure 13:
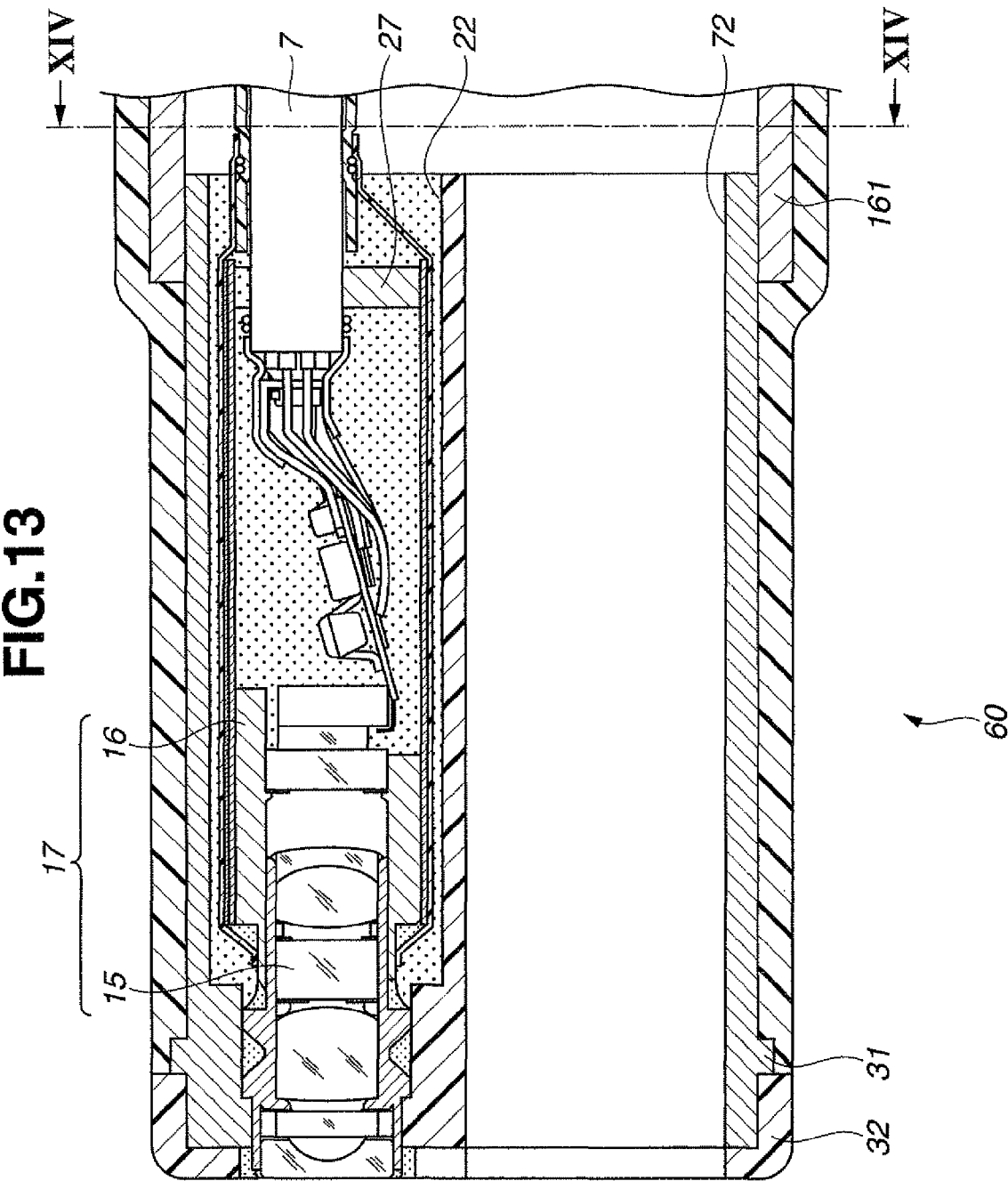
FIG. 13 is a sectional view of the distal end portion provided with an image pickup apparatus in which the extending position of the signal line is regulated.

The reinforcing frame 9 is positioned with respect to the objective lens unit 15 via the holding frame 11, and hence the extending position of the signal line 7 is positioned with respect to the objective lens unit 15. For example, there is shown in FIG. 13 a sectional view in the case where the image pickup apparatus 17, in which the extending position of the signal line 7 is positioned as shown in FIG. 11, is arranged in the distal end portion 60. In the image pickup apparatus mounting hole 22 of the distal end member 31, the image pickup apparatus 17 is arranged in the state where the extending position of the signal line 7 is offset in the radial direction to the outside of the distal end member 31 so as to be positioned. FIG. 14a shows an arrangement of built-in components in a bending portion 161 arranged at the proximal end side of the distal end member 31 in this case. Further, FIG. 14b shows an arrangement of the built-in components in the bending portion 161 at the time of using the image pickup apparatus in which the extending position of the signal line 7 is not positioned by being offset in the radial direction.

As shown in FIG. 14, the image pickup apparatus 17, a light guide 71b, an air supply and water supply channel 74b, and the forceps channel 72 are inserted into the bending portion 161 in addition to the signal line 7. The distance D1 between the signal line 7 and the forceps channel 72 at the time when the extending position of the signal line 7 is positioned by being offset in the radial direction to the outside of the distal end member 31, is larger than the distance D2 between the signal line 7 and the forceps channel 72 at the time when the extending position of the signal line 7 is not positioned by being offset in the radial direction. For this reason, it is possible to make the treatment tool insertion tube which is a built-in component to be inserted into the forceps channel 72, hardly interfere with the signal line 7 in the bending portion 161.

Further, in some layouts of arranging the built-in components, the signal line 7 may not interfere with the other built-in components in the bending portion 161. In this case, it is possible to reduce the bending amount of the signal line 7 at the time of bending the bending portion 161, by such a way that the extending position of the signal line 7 is positioned by being offset in the radial direction to the central side of the distal end member 31.

As described above, it is possible to improve the durability of the signal line 7 by positioning the extending position of the signal line 7 extended in the direction of the proximal end from the image pickup apparatus 17 with the signal line positioning member 27.

INDUSTRIAL APPLICABILITY

According to an electronic endoscope of the present invention, it is possible for the user of the electronic endoscope to replace the image pickup apparatus of the electronic endoscope with an image pickup apparatus of different specification, without separately purchasing an electronic endoscope of different specification.

The invention claimed is:
1. An electronic endoscope comprising:
an image pickup apparatus having a distal end and a proximal end that define a longitudinal axis of the image pickup apparatus, the image pickup apparatus comprising:
an objective lens unit comprising:
an objective lens for forming an image of light from an object; and
an objective lens frame for holding the objective lens; and
an image pickup device unit comprising:
a solid-state image pickup device arranged at an image forming position of the objective lens; and
a holding frame for holding the solid-state image pickup device;
a distal end member provided at a distal end portion of an insertion portion of the electronic endoscope, wherein the distal end member comprises a housing portion for housing the image pickup apparatus; and
an adjusting member provided between the housing portion of the distal end member and the image pickup apparatus, wherein the adjusting member is configured to hold the image pickup apparatus and is configured to be fixed in the housing portion,
wherein the adjusting member is separable from the image pickup apparatus,
wherein the adjusting member comprises:
a fitting portion shape adjusting member for holding at least one of the objective lens unit and the image pickup device unit in the housing portion, and for positioning the image pickup apparatus at a predetermined position in the housing portion by fitting into an outer peripheral of the image pickup apparatus and fitting to inside of the housing portion,
an external shape adjusting member for surrounding the outer peripheral of the image pickup apparatus and making a clearance between the housing portion and the image pickup apparatus a predetermined width, and
an adhesive for fixing the image pickup apparatus in the housing portion, the adhesive being filled between the housing portion and the external shape adjusting member, and
wherein the adjusting member is separated into a plurality of members including the fitting portion shape adjusting member and the external shape adjusting member, and the external shape adjusting member comprises a plurality of members separated by at least one plane substantially parallel to the longitudinal axis of the image pickup apparatus.

2. An electronic endoscope comprising:
an image pickup apparatus having a distal end and a proximal end that define a longitudinal axis of the image pickup apparatus, the image pickup apparatus comprising:
an objective lens unit comprising:
an objective lens for forming an image of light from an object; and
an objective lens frame for holding the objective lens;
an image pickup device unit comprising:
a solid-state image pickup device arranged at an image forming position of the objective lens; and
a holding frame for holding the solid-state image pickup device; and
a distal end member provided at a distal end portion of an insertion portion of the electronic endoscope,
wherein the distal end member comprises a housing portion for housing the image pickup apparatus, and
wherein the signal line positioning member is configured to position the signal line at a position offset in a radial direction from a central axis of the housing portion; and
an adjusting member provided between the housing portion of the distal end member and the image pickup apparatus, wherein the adjusting member is configured to hold the image pickup apparatus and is configured to be fixed in the housing portion, wherein:
the adjusting member is separable from the image pickup apparatus, and
the adjusting member comprises:
a fitting portion shape adjusting member for holding at least one of the objective lens unit and the image pickup device unit in the housing portion, and for positioning the image pickup apparatus at a predetermined position in the housing portion by fitting into an outer peripheral of the image pickup apparatus and fitting to inside of the housing portion,
an external shape adjusting member for surrounding the outer peripheral of the image pickup apparatus and making a clearance between the housing portion and the image pickup apparatus a predetermined width, and
an adhesive for fixing the image pickup apparatus in the housing portion, the adhesive being filled between the housing portion and the external shape adjusting member
wherein the adjusting member is separated into a plurality of members including the fitting portion shape adjusting member and the external shape adjusting member, and the external shape adjusting member comprises a plurality of members separated by at least one plane substantially parallel to the longitudinal axis of the image pickup apparatus.

3. An electronic endoscope comprising:
an image pickup apparatus having a distal end and a proximal end that define a longitudinal axis of the image pickup apparatus, the image pickup apparatus comprising:
an objective lens unit comprising:
an objective lens for forming an image of light from an object; and
an objective lens frame for holding the objective lens;
an image pickup device unit comprising:
a solid-state image pickup device arranged at an image forming position of the objective lens, wherein the solid-state image pickup device comprises a circuit board; and a holding frame for holding the solid-state image pickup device;

a signal line electrically connected to the circuit board of the solid-state image pickup device; and a signal line positioning member configured to position the signal line;

a distal end member provided at a distal end portion of an insertion portion of the electronic endoscope, wherein the distal end member comprises a housing portion for housing the image pickup apparatus, and wherein the signal line positioning member is configured to position the signal line at a position offset in a radial direction from a central axis of the housing portion; and an adjusting member provided between the housing portion of the distal end member and the image pickup apparatus, wherein the adjusting member is configured to hold the image pickup apparatus and is configured to be fixed in the housing portion, wherein the adjusting member is separable from the image pickup apparatus, wherein the adjusting member comprises:

a fitting portion shape adjusting member for holding at least one of the objective lens unit and the image pickup device unit in the housing portion, and for positioning the image pickup apparatus at a predetermined position in the housing portion by fitting into an outer peripheral of the image pickup apparatus and fitting to inside of the housing portion, an external shape adjusting member for surrounding the outer peripheral of the image pickup apparatus and making a clearance between the housing portion and the image pickup apparatus a predetermined width, and an adhesive for fixing the image pickup apparatus in the housing portion, the adhesive being filled between the housing portion and the external shape adjusting member, and wherein the adjusting member is separated into a plurality of members including the fitting portion shape adjusting member and the external shape adjusting member, and the external shape adjusting member comprises a plurality of members separated by at least one plane substantially parallel to the longitudinal axis of the image pickup apparatus.

* * * * *